US00PP32884P2

(12) United States Plant Patent
Koot

(10) Patent No.: US PP32,884 P2
(45) Date of Patent: Mar. 9, 2021

(54) POINSETTIA PLANT NAMED 'DOPOINJADWHIPE'

(50) Latin Name: *Euphorbia hybrida (Euphorbia pulcherrima X Euphorbia cornastra)*
Varietal Denomination: Dopoinjadwhipe

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/873,892

(22) Filed: Aug. 4, 2020

(51) Int. Cl.
*A01H 6/38* (2018.01)
*A01H 5/02* (2018.01)

(52) U.S. Cl.
USPC ..... Plt./304

(58) Field of Classification Search
USPC ..... Plt./304
See application file for complete search history.

(56) References Cited

PUBLICATIONS

PLUTO Plant Variety Datbase Sep. 24, 2020. p. 1.*

* cited by examiner

*Primary Examiner* — Annette H Para
(74) *Attorney, Agent, or Firm* — C. Anne Whealy

(57) ABSTRACT

A new and distinct cultivar of *Poinsettia* plant named 'Dopoinjadwhipe', characterized by its upright to somewhat outwardly spreading and uniformly mounding plant habit; moderately vigorous growth habit; moderately strong lateral branches; relatively early flowering habit; inflorescences with white-colored flower bracts; and excellent post-production longevity.

1 Drawing Sheet

Botanical designation: *Euphorbia hybrida* (*Euphorbia pulcherrima* X *Euphorbia cornastra*).
Cultivar denomination: 'DOPOINJADWHIPE'.

CROSS-REFERENCE TO A RELATED APPLICATION AND STATEMENT REGARDING PRIOR DISCLOSURES BY INVENTOR AND APPLICANT

This application claims priority to a European Community Plant Breeders' Rights application filed on Feb. 26, 2020, application number 2020/0593. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Poinsettia* plant, botanically known as *Euphorbia hybrida*, and hereinafter referred to by the name 'Dopoinjadwhipe'.

The new *Poinsettia* plant is a product of a planned breeding program conducted by the Inventor in Rheinberg, Germany. The objective of the breeding program is to create moderately vigorous *Poinsettia* plants with strong lateral branches and attractive flower bract coloration.

The new *Poinsettia* plant is a naturally-occurring whole plant mutation of *Euphorbia hybrida* 'Duepojadopin', disclosed in U.S. Plant Pat. No. 30,919. The new *Poinsettia* plant was discovered and selected by the Inventor as a flowering plant from within a population of plants of 'Duepojadopin' in a controlled greenhouse environment in Rheinberg, Germany in December, 2019.

Asexual reproduction of the new *Poinsettia* plant by terminal vegetative cuttings in a controlled greenhouse environment in Rheinberg, Germany since January, 2020 has shown that the unique features of this new *Poinsettia* plant are stable and reproduced true to type in successive generations of asexual reproduction.

SUMMARY OF THE INVENTION

Plants of the new *Poinsettia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Dopoinjadwhipe'. These characteristics in combination distinguish 'Dopoinjadwhipe' as a new and distinct *Poinsettia* plant:

1. Upright to somewhat outwardly spreading and uniformly mounding plant habit.

2. Moderately vigorous growth habit.
3. Moderately strong lateral branches.
4. Relatively early flowering habit.
5. Inflorescences with white-colored flower bracts.
6. Excellent post-production longevity.

Plants of the new *Poinsettia* differ primarily from plants of the mutation parent, 'Duepojadopin', in the following characteristics:

1. Plants of the new *Poinsettia* are more compact than and not as vigorous as plants of 'Duepojadopin'.
2. Plants of the new *Poinsettia* have white-colored flower bracts whereas plants of 'Duepojadopin' have pink-colored flower bracts.

Plants of the new *Poinsettia* can be compared to plants of *Euphorbia pulcherrima* Willd. ex Klotzsch X *Euphorbia cornastra* 'Bonpri 974', disclosed in U.S. Plant Pat. No. 27,689. In side-by-side comparisons, plants of the new *Poinsettia* differ primarily from plants of 'Bonpri 974' in the following characteristics:

1. Plants of the new *Poinsettia* are larger than plants of 'Bonpri 974'.
2. Plants of the new *Poinsettia* have longer lateral branches than plants of 'Bonpri 974'.
3. Branching habit of plants of the new *Poinsettia* is more upright than branching habit of plants of 'Bonpri 974'.

BRIEF DESCRIPTION OF THE PHOTOGRAPH

The accompanying photograph illustrates the overall appearance of the new *Poinsettia* plant showing the colors as true as it is reasonably possible to obtain in colored reproductions of this type. Colors in the photograph may differ slightly from the color values cited in the detailed botanical description which accurately describe the colors of the new *Poinsettia* plant. The photograph is a side perspective views of a typical flowering plant of 'Dopoinjadwhipe' grown in a container.

DETAILED BOTANICAL DESCRIPTION

The aforementioned photograph and following observations and measurements describe plants grown in Rheinberg, Germany during the summer and autumn in 13-cm containers in a glass-covered greenhouse and under cultural practices typical of commercial *Poinsettia* production. During the production of the plants, day and night temperatures averaged 18° C. and light levels averaged 4,500 lux. Single plants were grown in 13-cm containers and were pinched one time about three weeks after planting the rooted young plants. Plants were 23 weeks old when the photograph and the detailed description were taken. In the following description, color references are made to Pantone Color Chart, 2015 Edition, except where general terms of ordinary dictionary significance are used.

Botanical classification: *Euphorbia hybrida* 'Dopoinjadwhipe'.

Parentage: Naturally-occurring whole plant mutation of *Euphorbia hybrida* 'Duepojadopin', disclosed in U.S. Plant Pat. No. 30,919.

Propagation:

*Type*.—Terminal vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Uniform, upright and mounded plant habit; inverted triangle; large inflorescences with numerous flower bracts positioned above the foliar plane; moderately vigorous growth habit.

*Plant height*.—About 23 cm.

*Plant diameter or spread*.—About 34.5 cm.

*Lateral branch description*.—Quantity: Freely branching habit with lateral branches potentially developing at every node after pinching; upright branching habit. Length: About 17.5 cm. Diameter: About 3 mm. Internode length: About 1.5 cm. Strength: Moderately strong. Texture: Smooth, glabrous. Luster: Moderately glossy. Color: Close to 137A.

*Leaf description*.—Arrangement: Alternate, simple. Length: About 8.7 cm. Width: About 4.4 cm. Shape: Ovate. Apex: Apiculate. Base: Obtuse. Margin: Irregularly lobed; slightly undulate. Aspect: Horizontal to drooping; keeled. Texture, upper surface: Smooth, glabrous. Texture, lower surface: Rugose, glabrous; prominent venation. Luster, upper and lower surfaces: Matte. Venation pattern: Pinnate, arcuate. Color: Developing leaves, upper surface: Close to 137A. Developing leaves, lower surface: Close to 138A. Fully developed leaves, upper surface: Close to 139A; venation, close to 146A. Fully developed leaves, lower surface: Close to 137A to 137B; venation, close to 146B to 146C. Leaf petioles: Length: About 4.1 cm. Diameter: About 2 mm. Texture, upper and lower surfaces: Smooth, glabrous. Luster, upper and lower surfaces: Matte. Color, upper surface: Close to 141C. Color, lower surface: Close to 141D.

Inflorescence description:

*Inflorescence type and habit*.—Terminal inflorescences are compound corymbs of cyathia with numerous colored flower bracts subtending the cyathia; inflorescences uniformly positioned above the foliar plane.

*Fragrance*.—None detected.

*Flowering response*.—Under natural season conditions, plants typically flower in October and November; under artificial long nyctoperiod/short photoperiod conditions, plants flower about eight weeks later.

*Post-production longevity*.—Good post-production longevity; plants of the new *Poinsettia* maintain good substance and flower bract color for about five to twelve weeks under interior conditions; flower bracts persistent and cyathia not persistent.

*Inflorescence diameter, without flower bracts*.—About 1.7 cm.

*Inflorescence height, without flower bracts*.—About 2 cm.

*Flower bracts*.—Quantity per inflorescence: Numerous, about 14. Length, largest bracts: About 8.4 cm. Width, largest bracts: About 3.9 cm. Shape: Ovate. Apex: Apiculate. Base: Obtuse. Margin: Irregular lobing. Aspect: Flat, horizontal; keeled. Texture, upper surfaces: Smooth, glabrous. Texture, lower surface: Rugose, glabrous; prominent venation. Luster, upper and lower surfaces: Matte. Venation pattern: Pinnate, arcuate. Color: Developing bracts, upper surface: Close to N155D. Developing bracts, lower surface: Close to 155C. Fully developed bracts, upper and lower surfaces: Close to 155C; venation, close to 155C. Bract petioles: Length: About 2 cm. Diameter: About 1 mm. Texture, upper and lower surfaces: Smooth, glabrous. Color, upper surface: Close to 186D. Color, lower surface: Close to 141D.

*Cyathia*.—Quantity per corymb: About eight. Length: About 8 mm. Width: About 6 mm. Shape: Ovoid. Texture: Smooth, glabrous. Color: When developing, inner surface: Close to 143C. When developing, outer surface: Close to 143B. Fully developed, inner surface: Close to 143B. Fully developed, outer surface: Close to 143B to 143C.

*Nectaries*.—Quantity per cyathium: One. Length: About 4 mm. Width: About 1 mm. Shape: Oval. Texture: Smooth, glabrous. Color: When developing and fully developed, inner surface: Close to 17A. When developing and fully developed, outer surface: Close to 17C.

*Peduncles*.—Length: About 4 mm. Diameter: About 1 mm. Strength: Strong. Aspect: Incurved. Texture: Smooth, glabrous. Color: Close to 143C.

*Reproductive organs*.—Stamens: Quantity per cyathium: About 20. Filament length: About 7 mm. Filament color: Close to 53A. Anther shape: Oval. Anther length: About 0.5 mm. Anther color: Close to 187A to 187B. Amount of pollen: Abundant. Pollen color: Close to 9A. Pistils: Quantity per cyathium: One; tri-parted. Pistil length: About 1 cm. Stigma shape: Crested. Stigma color: Close to 59A to 59B. Style length: About 2 mm. Style color: Close to 144B. Ovary color: Close to 144A. Fruits & seeds: To date, fruit and seed development has not been observed on plants of the new *Poinsettia*.

Pathogen & pest resistance: Plants of the new *Poinsettia* have not been shown to be resistant to pathogens and pests common to *Poinsettia* plants to date.

Temperature tolerance: Plants of the new *Poinsettia* have been observed to tolerate temperatures ranging from about 12° C. to about 40° C.

It is claimed:

1. A new and distinct *Poinsettia* plant named 'Dopoinjadwhipe' as illustrated and described.

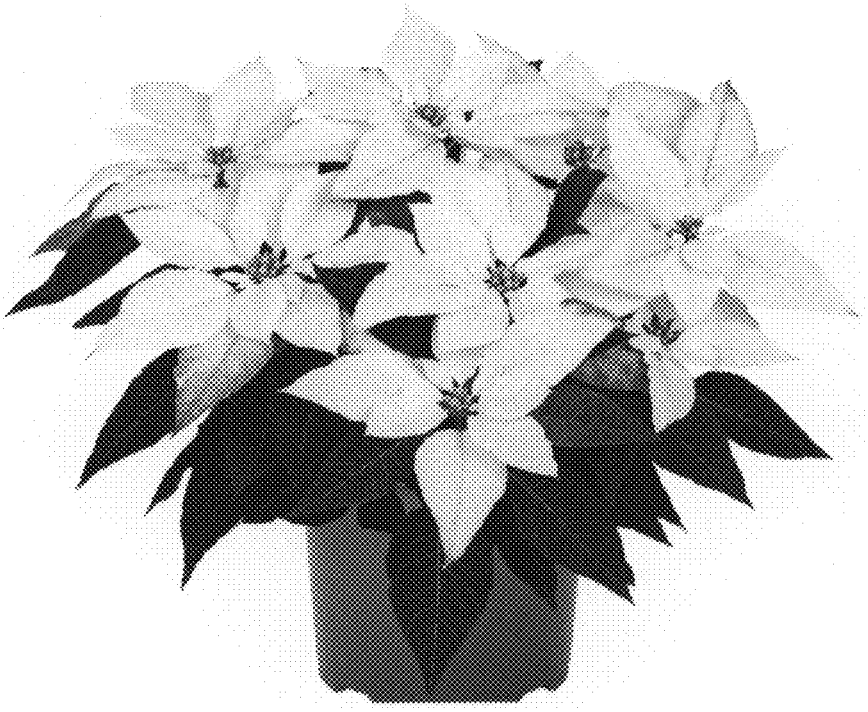

* * * * *